United States Patent
Gray et al.

(10) Patent No.: US 7,030,104 B2
(45) Date of Patent: Apr. 18, 2006

(54) TOPICAL OESTROPROGESTATIONAL COMPOSITIONS WITH A SYSTEMIC EFFECT

(75) Inventors: Georges Gray, Monoco (MC); Bertrand Villet, Antibes (FR); Jacques Paris, Nice (FR); Jean-Louis Thomas, Charenton-le-Pont (FR)

(73) Assignee: Laboratoire Theramex, (MC)

( * ) Notice: Subject to any disclaimer, the term of this patent is extended or adjusted under 35 U.S.C. 154(b) by 79 days.

(21) Appl. No.: 10/129,040

(22) PCT Filed: Sep. 14, 2001

(86) PCT No.: PCT/FR01/02865

§ 371 (c)(1),
(2), (4) Date: Jun. 26, 2002

(87) PCT Pub. No.: WO02/22132

PCT Pub. Date: Mar. 21, 2002

(65) Prior Publication Data

US 2003/0181430 A1    Sep. 25, 2003

(30) Foreign Application Priority Data

Sep. 15, 2000    (FR) .................................. 00 11791

(51) Int. Cl.
*A61K 31/56* (2006.01)
*A61K 9/14* (2006.01)
*A61K 9/00* (2006.01)

(52) U.S. Cl. ...................... 514/170; 424/400; 424/484; 424/485; 514/178; 514/182

(58) Field of Classification Search ................ 514/170, 514/178, 182; 424/485, 484, 400
See application file for complete search history.

(56) References Cited

U.S. PATENT DOCUMENTS 4,379,454 A * 4/1983 Campbell et al.

FOREIGN PATENT DOCUMENTS

FR    2 776 191 A1 *  9/1999
WO    WO 98/15279    * 4/1998

* cited by examiner

*Primary Examiner*—Shengjun Wang
(74) *Attorney, Agent, or Firm*—Charles A. Muserlian (57) ABSTRACT

The present invention relates to the field of therapeutic chemistry and more especially to the realization of new galenic forms intended to be applied on the skin.

More particularly it relates to a topical hormonal composition with a systemic effect for the hormonal treatment of the perimenopause and of the menopause as well as for the treatment of the ovarian hormonal deficiencies in women with amenorrhea, characterized in that it comprises, as active ingredients, a progestogen derived from 19-nor progesterone and estradiol or one of its derivatives, a vehicle which allows the systemic passage of said active ingredients, chosen from the group constituted by a solubilizing agent, an absorption promoting agent, a film-forming agent, a gelling agent and their mixtures, in combination or in a mixture with suitable excipients for the realization of a gelled and/or film-forming pharmaceutical form.

25 Claims, 1 Drawing Sheet

TOPICAL OESTROPROGESTATIONAL COMPOSITIONS WITH A SYSTEMIC EFFECT

This application is a 371 of PCT/FR01/02865 filed Sep. 14, 2001.

The present invention relates to the field of therapeutic chemistry and more especially to the realization of new galenic forms intended to be applied on the skin.

A more particular subject of the present invention is cutaneous topical preparations the active ingredients of which are a synthetic progestogen and a natural or synthetic estrogen and the penetrating power of which makes it possible to obtain a systemic hormonal effect.

The invention relates more specifically to a topical estrogen-progestogen composition with a systemic effect for the hormonal treatment of the perimenopause and of the menopause as well as for the treatment of ovarian hormonal deficiencies in women with amenorrhea.

The French patent FR 2 737 411 and the French patent FR 2 754 179 in the name of the Applicant already describes estrogen-progestogen compounds intended for administration by oral route.

However, in the same way for the progestogens as for the oestrogens, the oral route does present some drawbacks. On the one hand, it requires the administration of large doses in order to compensate for the degradation of the active ingredients during passage through the intestines and the liver (so-called <<first pass>> effect). On the other hand, it does not lead to constant plasmatic levels over time as oral administration is followed by a plasmatic peak during the which blood concentrations are transitionally high.

Estradiol and some of its derivatives as well as certain synthetic progestogens are administered by percutaneous route in order to obtain either a substitution within the context of a replacement hormone treatment, or a contraceptive action. However, it requires, particularly for the progestogens, the use of specific galenic forms such as patches combining occlusion, solubilizing agents and powerful passage promoters in order to obtain the plasmatic levels necessary for a systemic effect. These technical solutions are not available for all the progestogens. In addition, the active ingredients interact on the respective percutaneous passage. Because of this, the previously described preparations for the percutaneous passage of a single synthetic progestogen agent, such as described in the French Patent Application published under N° 2 776 191 in the name of the Applicant, are not directly applicable to an estrogen-progestogen combination as each combination of this type requires a specific galenic solution.

The function of the protective barrier of the skin against external aggressions makes it hard to permeate vis-à-vis a number of substances and does not allow medicinal molecules to penetrate except under certain conditions: size and nature of the molecule, solubility, stability, nature of the vehicle containing the molecule; thickness of the skin, state of hydration, pathological condition, location.

Therefore, the release of an active ingredient from a vehicle and its penetration through the skin to the blood or lymphatic circulation depends on a number of physico-chemical and physiological parameters, which are rarely combined or have not yet been defined.

In the present invention, the nature of one of the 2 active ingredients itself, namely synthetic progestogen, represents the main obstacle to percutaneous penetration; thus, the major problem posed for progestogen is its poor diffusion through the epidermis because of its lipophilic nature. A second difficulty lies in the interaction between the two active ingredients vis-à-vis percutaneous passage. The choice of the vehicle used in the compositions according to the invention is therefore of great importance in percutaneous the penetration and the therapeutic activity of the active ingredients.

The topical compositions according to the invention make it possible to obtain a systemic effect by optimization of the percutaneous passage of a synthetic progestogen derived from 19-nor progesterone and a natural or synthetic oestrogen, combined in the same composition.

A more specific subject of the present invention is therefore a topical hormonal composition with a systemic effect for the hormonal treatment of the perimenopause and of the menopause as well as for the treatment of ovarian hormonal deficiency in women with amenorrhea, in the form of a gel or a solution, characterized in that it comprises:

as active ingredients, a progestogen derived from 19-nor progesterone and an oestrogen, natural or synthetic
as well as a vehicle allowing the systemic passage of said active ingredients chosen from the group constituted by a solubilizing agent, an absorption promoting agent, a film-forming agent, a gelling agent and their mixtures, in combination or in a mixture with suitable excipients for the realization of a gelled and/or film-forming pharmaceutical form.

The compositions according to the invention may be in the form of a gel, a film-forming gel or a film-forming solution.

The progestogen derived from 19-nor progesterone used in the present invention is nomegestrol and/or one of its esters or one of its ethers. An example of nomegestrol ether is nomegestrol tetrahydropyranic ether. An example of nomegestrol ester is nomegestrol acetate.

The oestrogen used in the present invention is 17beta estradiol or one of its esters or ethers. An example of a fatty acid ester of estradiol is estradiol valerate. An example of an estradiol ether is promestriene (17-methyl and 3-propyl ethers of estradiol).

Administered in the compositions according to the invention, nomegestrol acetate and estradiol are capable of going through the skin and passing into the blood circulation in order to produce plasmatic levels which can be detected using methods used to determine it in biological mediums.

The plasmatic levels of estradiol and nomegestrol acetate obtained with the compositions which are the subject of the present invention are able to induce a hormonal effect on the tissues located at a distance from the application site and in particular on the endometrium.

The combination of estradiol and nomegestrol acetate, thus administered in a repeated manner, produces a therapeutic action when it is applied in non-menopausal women suffering from an estrogen-progestogen deficiency or in menopausal women who are candidates for hormone replacement therapy.

According to the present invention, nomegestrol or one of its esters or ethers is present in a quantity varying from 0.05 to 5.0%, and preferably from 0.05 to 1.5% by weight of the total composition. The estradiol or one of its esters or ethers is present in a quantity varying from 0.05 to 1.0% by weight of the total composition, and preferably from 0.05 to 0.5% by weight.

In a more preferred manner, nomegestrol or one of its esters or ethers is present in a quantity varying from 0.1 to 2% by weight of the total composition and estradiol or one of its esters or ethers in a quantity varying from 0.1 to 0.3% by weight of the total composition, with a preference for a concentration of nomegestrol or one of its esters or ethers varying from 0.1 to 1% and estradiol from 0.01 to 0.2%.

Topical compositions with a systemic effect currently preferred according to the invention are those containing a quantity of nomegestrol or of one of its esters or ethers of the order of 1.0% by weight of the total composition, and a quantity of estradiol or of one of its esters or ethers of the order of 0.15% by weight of the total composition.

The solubilizing agents and the absorption promoting agents have different modes of action but both make it possible to encourage the penetration of active ingredients through the skin The solubilizing agents, by acting on the thermodynamic activity of the active molecule, improve the solubility of the active ingredient and modify its affinity for the cutaneous structures, in particular the stratum corneum. The absorption promoting agents reduce the resistance to diffusion of the cutaneous barrier by modifying its structure.

The Solubilizing Agents

The solubilizing agents increase the solubility of the active ingredients but there is however no direct relationship between improvement in the solubility of the active ingredient in the vehicle and its increased percutaneous passage. In fact, the agents which improve the solubility of an active ingredient also increase its affinity for the vehicle and can therefore definitively reduce its diffusion through the skin.

For an active ingredient to be completely solubilized in a vehicle, it must have a defined affinity for it; nevertheless, this affinity must not be so great that the partition coefficient of the active ingredient encourages its diffusion through the skin. According to the present invention, the choice of solvents and their concentrations ensures adequate dissolving and percutaneous passage of each of the two active ingredients.

According to the present invention, appropriate examples of solubilizing agents are alcohols, wateralcohol mixtures, propyleneglycol, polyethyleneglycol, polyethylene 20 sorbitan mono-oleate [marketed for example under the name Polysorbate 80 DF], a glycosylated polyoxyethylenated $C_8/C_{10}$ glyceride (marketed for example under the name Labrasol®). As a solubilizing agent, a mixture of the aforementioned solvents and/or solubilizing agents is generally used, which, thanks to a synergy of action, is more effective that each of them used alone.

Preferably, the solubilizing agent is chosen from the group consisting of water, alcohols, propyleneglycol or their mixtures.

An example of a suitable solubilizing agent for the topical composition with a systemic effect according to the invention is the ethanol/water/propyleneglycol ternary mixture, in which the quantity of ethanol varies from 30 to 60% by weight of the total composition, the quantity of water varies from 20 to 60% by weight of the total composition, and more particularly from 30 to 60% by weight, and that of propyleneglycol from 2 to 20% by weight of the total composition.

More particularly, a suitable solubilizing agent for the composition according to the invention is the mixture comprising 40 to 60% ethanol, 25 to 45% water and 6 to 12% propyleneglycol, and in particular from 40 to 50% ethanol, from 40 to 45% water and from 6 to 12% by weight propyleneglycol.

The Absorption Promoting Agents

The absorption promoting agents are substances capable of improving the diffusion of active ingredients in the epidermis, in particular the stratum corneum. These adjuvants can be classified in different families according to their chemical structure. As an example of absorption promoting agents, dioxolane derivatives such as isopropylidene glycerol, marketed under the name Solketal (which is also an excellent solubilizing agent for the hormones of this invention) or 2n-nonyl 1–3 dioxolane; or diethylene glycol monoethyl ether (for example that marketed under the Tradename Transcutol®) can in particular be mentioned. Absorption promoting agents are also described in the following chemical families: polyols, fatty acids, esters of fatty acids alcohols and amides. As an example of substances representative of these families, propylene glycol monocaprylate or Capryol 90, caprylic acid, diisopropyl adipate, polysorbate 80, 2-octyl dodecanol and 1-dodecylazacyclohepta-2-one or Azone, can in particular be mentioned. Substances presenting properties of absorption promoting agents can also be found in the family of sulphoxides (such as for example dimethylsulphoxide), terpenes (for example d-limonene), alkanes (for example N-heptane) or organic acids (salicylic acid and salicylates in particular).

The absorption promoting agent, more particularly suitable in the present invention, is selected from the dioxolane group, such as for example isopropylideneglycerol (Solketal) or from the group of long chain $C_6$ to $C_{18}$ fatty acids such as lauric acid, caprylic acid or oleic acid.

The quantity of absorption promoting agent in the compositions according to the invention, varies from 2 to 12% by weight of the total composition.

An absorption promoting agent particularly suitable in the compositions according to the invention is isopropylideneglycerol; the quantity of isopropylideneglycerol is preferably from 3 to 8% by weight of the total composition, and in a more preferred manner from 3 to 6% by weight.

Gelling Agents

The choice of gelling agents and film-forming agents is also important in the compositions according to the invention.

Gelling agents are substances which thicken and modify the viscosity of a liquid vehicle, thus constituting a gel in the form of a three-dimensional colloidal network. There are several types of gelling agent: natural gelling agents (mineral, vegetable, animal), synthetic agents and semi-synthetic agents.

Examples of natural gelling agents are guar gum, algae extract (alginates, carrageenates, gelose), polysaccharides (xanthan gum, arabic gum, tragacanth gum), starches, pectins, etc.

Examples of synthetic or semi-synthetic gelling agents are cellulose derivatives, in particular those obtained by esterification or by etherification of cellulose, and acrylic derivatives. In the category of acrylic derivatives, are carbomers, polycarbophiles and acrylates.

According to the present invention, the gelling agent is preferably chosen from the group consisting of cellulose derivatives and acrylic derivatives.

Among the cellulose derivatives, they are the methylcelluloses (Methocel, Metolose), ethylcelluloses (Ethocel, Aquacoat®), hydroxypropylmethylcelluloses (Kenal, Methocel, Hypromelose), hydroxyethylcelluloses (Cellosize, Natrosol), hydroxypropylcelluloses (Klucel), carboxymethylcelluloses, cross-linked or not, in sodium or calcium form (Akucell, Nymcel, Tylose CB, Croscarmellose, Acdisol).

Among the acrylic derivatives, carbomers can notably be mentioned, in particular those marketed under the names Carbopol® or Synthalen®. According to the invention the preferred carbomers are those that form gels which <<break down>> most easily on contact with electrolytes and the skin.

The carbomers produce formulations which are stable over time and give the formulation rheological properties which can be reproduced because of their synthetic nature.

The existence of different degrees or grades for the products depends on differences in molecular weight, the degree of cross-linking, the nature of the molecular arrangements and the polymerization solvent.

Therefore, from the different grades of carbomer, those marketed by the Goodrich Company under the names Carbopol 974 P®, Carbopol 980®, Carbopol 1382® and Carbopol 2020®, or similar products such as the Synthalens from 3 V France, such as Synthalen K, L, M or preneutralised, such as for example Synthalen PNC®, can be mentioned.

According to the present invention, the carbomer marketed under the name Carbopol 1382® is particularly suitable as it liquefies on contact with the electrolytes of the skin and thus avoids a polymer deposit which risks being an obstacle to the passage of the active ingredients. The quantity of Carbopol 1382 is preferably from 0.3 to 1% by weight of the total composition.

The Film-Forming Agents

The film-forming agents used are those which are used to realize coating or filming wrapping solutions as each of them are mainly the product of the food or biomedical industry. They make it possible to envisage a cutaneous application with a view to realizing an occlusive film at skin level, preserving a cutaneous hydration known to encourage percutaneous passage. In addition, the film-forming agents make it possible to give the formulation a more pleasant feel.

The film-forming agents can be classed in different groups according to their solubility. According to the present invention, the film-forming agent is selected from the group consisting of silicones, cellulose derivatives, methacrylic derivatives and polyvinylpyrrolidone derivatives.

The silicones used according to the invention can be soluble or insoluble in water. According to the present invention, silicone is chosen from the group constituted by dimethicone, dimethiconol, simethicone, their mixtures, and more particularly:

the mixture of stearoxytrimethylsilane and stearic alcohol marketed under the name of Silky Wax 10 (Dow Corning) in the presence or not of an emulsifier such as laurylmethicone, the dimethiconol (hydroxy(n-blocked)polydimethylsiloxane) mixture in dimethicone (polydimethyl-siloxane) marketed under the name DC Blend 20.

The quantity of silicone varies from 1 to 3% by weight of the total composition.

In the present invention, the silicone which is particularly suitable is that marketed under the name DC Blend 20; the quantity of DC Blend 20 which is particularly suitable is of the order of 2% by weight of the total composition.

Among the cellulose derivatives, the following can be mentioned:

hydroxypropylmethylcellulose acetate succinate, and in particular that marketed by the Seppic Company under the name Aqoat AS-LF®, an aqueous dispersion of cellulose acetophthalate containing 70% water, 23% cellulose acetophthalate and 7% poloxamer, and in particular that marketed by the Seppic Company under the name Aquacoat CPD®, an aqueous dispersion of ethylcellulose, cetyl alcohol and sodium lauryl sulphate, in particular that marketed by the Seppic Company under the name Aquacoat ECD 30®, ethylcellulose.

Among the methacrylic derivatives, the following can be mentioned:

an aqueous dispersion of an anionic copolymer of methacrylic acid and ethyl acrylate (type C), in particular that containing 30% dry copolymer, 0.7% of sodium lauryl sulphate and 2.3% Polysorbate 80 NF, marketed under the name Eudragit L30 D55® (Rohm and Haas), an acrylic acid and methacrylic ester (type A) copolymer, in particular that marketed under the name Eudragit RL 100® (Rohm and Haas).

Among the polyvinylpyrrolidone derivatives, the following can be mentioned:

a povidone, the molecular weight of which is of the order of 360 000, marketed under the name Kollidon 90® the polyvinylpyrrolidone/vinyl acetate 64 copolymer, of formula $(C_6H_9NO)_n \times (C_4H_6O_2)_m$ the molecular weight of which is: $(111.1)_n \times (86.1)_m$.

the homopolymers of polyvinyl alcohol.

The other Excipients of the Composition

The topical hormonal compositions with a systemic effect according to the invention can moreover contain other excipients which are complexing agents, neutralizing agents such as disodium edetate (EDTA), neutralising agents such as triethanolamine (TEA) and/or plasticizers such as diethyl phthalate and triacetin.

A particularly suitable topical hormonal composition according to the invention is a composition which is in the form of a gel and which contains in particular, in a hydroalcoholic mixture, 0.4% nomegestrol acetate, 0.15% estradiol, 8% propyleneglycol, 3% isopropylideneglycerol and 2% silicone DC Blend 20.

Preferably, the compositions according to the invention have a pH of between 6 and 7 and a viscosity ranging between 1000 and 2000 mPas.

The invention also relates to processes for the preparation of topical estrogen-progestogen compounds with a systemic effect.

A process for the preparation of the compositions in the form of a gel is given below as an example.

The important stages in the preparation of a gel are the dispersion of the gelling agent in the solubilizing agent (the dispersion of which will considerably influences the quality of the obtained preparation), agitation, hydration, swelling and finally gelation.

Dispersion and Agitation: Wetting

The gelling agent (acrylic derivative) is placed in suspension under agitation in the solvent (solubilizing agent). The agitation must be moderate as the acrylic polymer loses its gelling power if the shear is too great.

Hydration and Swelling of the Polymers

In order to avoid the formation of partially hydrated clusters, the incorporation of the polymers by sieving them is recommended, to facilitate the wettability and the hydration of the powder and allows them to arrange themselves in a network. This stage is encouraged by wetting the powder beforehand in the solvent or in the most polar solvent if a solvent system is used.

Gelation: Neutralisation of the Dispersion Obtained

The pH of the suspension obtained during the previous stage is close to 3 (this pH is a function of the polymer concentration, and therefore of the carboxylic groups). The medium is neutralised by using mineral bases such as sodium, potassium or ammonium hydroxides when the formulation solvents are aqueous and organic bases such as the amines (triethanolamine, tromethamine or TRIS etc.) when they are slightly polar or non-polar. The addition of these agents causes a spontaneous thickening by formation of the polymer salts, soluble in the water.

A more particular example of preparing a gel according to the invention the gelling agent of which is an acrylic derivative, is characterized in that:

the active ingredients and the EDTA are solubilized in a water/95° ethanol/propyleneglycol solvent system whilst agitating at 300 rpm (approximately 30 min);

the acrylic polymer is dispersed in small fractions in the solution of active ingredients by agitating at 100 rpm;

the acrylic polymer is let to swell for 2 hours under agitation at 200 rpm;

the dispersion is neutralised by triethanolamine (TEA) dissolved in a fraction of water taken from the quantity to be incorporated in the formulation; the agitation is reduced to 100 rpm during neutralisation to avoid the incorporation of air bubbles;

agitation is carried out for 30 minutes at 50 rpm to homogenise the gel obtained.

The preparation of the compositions according to the invention in the form of film-forming gels (or filming gels) and film-forming solutions (or filming solutions) can also be envisaged.

Such forms are envisaged, as, during their application on the skin, they form, after drying, an occlusive film sufficient to increase the hydration of the skin and improve the diffusion of the active ingredients that they contain. The form obtained must nevertheless penetrate or dry rapidly whilst having a pleasant and non-sticky feel.

Therefore, an example of preparing a <<film-forming solution>> the film-forming agent of which is solid, is characterized in that:

the quantities of ethanol, water and propyleneglycol necessary for the formulation are agitated at 250 rpm for 10 min;

the EDTA and the active ingredients are solubilized in the mixture obtained;

the plasticizing agent is added and agitation is carried out at 250 rpm for 30 min;

the film-forming agent is dispersed in small fractions whilst maintaining the same agitation, until it is completely solubilized; agitation is continued for 1 hour;

the pH is adjusted using a solution of triethanolamine (TEA) dissolved in a small quantity of water, taken from the quantity of water to be incorporated into the formulation, whilst reducing the agitation to 100 rpm; the solution obtained is homogenized for 30 min.

Another example of preparing a <<film-forming solution>> the film-forming agent of which is in an aqueous dispersion, is characterized in that:

the water and a plasticizing agent are mixed at 250 rpm and agitated for 30 minutes;

the dispersion of the film-forming agent is added in small fractions whilst agitating at 250 rpm, until a homogenous solution is obtained; agitation is continued for 1 hour;

the EDTA and the active ingredients are solubilized independently in the ethanol and propyleneglycol mixture; agitation is carried out until total dissolution;

the alcoholic solution of active ingredients in the aqueous solution is added in small fractions under agitation at 250 rpm; the solution obtained is agitated for 1 hour to homogenise it;

the solution is neutralised with triethanolamine (TEA) dissolved in water, whilst reducing the agitation; the solution obtained is homogenized for 30 min.

The film-forming gels are obtained by gelation of the film-forming solutions. Two solutions are therefore prepared separately:

an aqueous solution containing a solubilized plasticizer, in which the film-forming agent is totally solubilized under vigorous agitation;

an alcoholic solution containing the other excipients of the formulation and in which the active ingredients are solubilized; and the gelling agent is dispersed and left to swell;

the alcoholic solution is mixed in the aqueous solution and the solution is gelled with triethanolamine.

The topical compositions according to the invention are intended to be applied on the skin generally on the abdomen, the arms, the thighs, and the buttocks etc.

EXPERIMENTAL PART

1) Evaluation In Vitro of the Percutaneous Passage of the Progestogen/Estrogen Active Ingredients In this part, the percutaneous passage in vitro of nomegestrol acetate and estradiol will more particularly be studied. A gel which contains exclusively nomegestrol acetate was studied previously and made it possible to obtain in women sufficient circulating levels to ensure an objectivized endometrial effect attested by bleedings. This test is described in the document FR 98.03533 in the name of the Applicant. Nevertheless, to guarantee efficacy in all women, it appeared worthwhile to increase the percutaneous flow of nomegestrol acetate in a system also capable of ensuring an adequate percutaneous flow of estradiol.

a) Principle

Percutaneous absorption is studied in vitro on static diffusion cells, called Franz cells™. The percutaneous passage of the active ingredients is evaluated by measuring the radioactivity using labelled molecules (carbon 14, tritium). The overall quantity of active ingredient absorbed is measured, at different times, in the receiving compartment.

b) Description of the Cell

A cutaneous biopsy is horizontally maintained between the two parts of the cell thus delimiting on both sides of the sample, two compartments: one of them epidermic, constituted by a glass cylinder, of a defined area (1.76 cm$^2$), placed on the upper surface of the skin; the other dermic (or receptor), on the underside of the biopsy, comprises a fixed volume reservoir with a side nozzle. The two compartments are kept in place through the intermediary of a clamp.

The receiving compartment is filled with a basal liquid constituted by a solution of isotonic phosphate buffer at pH 7.4 (Monosodium phosphate: 0.04 M; Disodium phosphate: 0.02 M; NaCl: 0.08 M, Albumin: 15 g/l). Samples of the liquid contained in the lower compartment are taken via the side nozzle during the course of the experiment and at the end of the test. Each time, the basal liquid is completely removed and replaced by new liquid. A dual circulation water jacket surrounds the underside of the cell and allows thermostatic temperature control of the assembly at a temperature of 37° C. The homogeneity of the contents of the receiving compartment is ensured by the movements of a magnetic stirrer. The upper part of the cell is open towards the outside thus exposing the surface of the epidermis to the ambient air of the laboratory as in the case of use in vivo.

c) Preparation of the Cutaneous Biopsies

The skin, of human origin, was taken from a healthy subject, at abdominal level, during the course of plastic surgery. The adhering sub-cutaneous fat is removed from the cutaneous samples using a scalpel.

d) Implementation of the Method

The preparations to be studied are applied in weighed quantities, using a spatula over all of the epidermal area circumscribed by the glass cone. At precise time intervals (2 hours, 4 hours, 6 hours, 8 hours, 10 hours, 24 hours), all of the liquid content in the receiving compartment is removed via the side nozzle and replaced by new liquid. The samples removed are treated with Pico-fluorine 40™ scintillation liquid and the activity measured using a liquid scintillation counter.

e) Determining the Radioactivity

Scintillation in a liquid medium was used to detect the β radiation emitted by the radioelements. The measurements are carried out using a Packard Tricarb 4435™ liquid scintillation counter.

f) Expression of the Results

The percutaneous passage of the active ingredients is evaluated at the time of each sampling by measuring the cumulative quantity (μg) of active ingredient as a function of time.

The average results correspond to four experimental determinations per formula and are associated with the standard deviation (S.D.).

2) Example 1: 1$^{st}$ Series of Gels

The Formulations Tested

The percutaneous passage of the 2 active ingredients was studied in vitro for the gels the formulae of which are listed in Table 1 (Table 1). These gels differ by their estradiol content, their content of solubilizing agent, the nature and the content of passage promoting agents and the ratio between solubilizing agents and passage promoting agents. For this 1$^{st}$ series of gels, the nomegestrol acetate concentration in the formulation is fixed at 0.4%.

TABLE 1

Percentage composition of the 1$^{st}$ series gels

| REFERENCE | G29-287 | G29-299 | Tx11323 batch-12 | G42-110 | G42-111 | G47-1 | G47-5 |
|---|---|---|---|---|---|---|---|
| NAc (nomegestrol acetate) | 0.4 | 0.4 | — | 0.4 | 0.4 | 0.4 | 0.4 |
| Estradiol | — | 0.1 | 0.1 | 0.15 | 0.1 | 0.2 | 0.15 |
| Carbopol 1342 or 1382 | 0.5 | 0.5 | 0.5 | 0.5 | 0.5 | 0.5 | 0.5 |
| Propyleneglycol | 6 | 6 | 6 | 8 | 8 | 8 | 6 |
| Transcutol | 5 | 5 | 5 | — | — | — | — |
| Solketal | | | | 3 | 3 | 3 | 5 |
| EDTA | 0.05 | 0.05 | 0.05 | 0.05 | 0.05 | 0.05 | 0.05 |
| Triethanolamine | 0.3 | 0.3 | 0.3 | 0.3 | 0.3 | 0.3 | 0.3 |
| Demineralized water | 42.75 | 42.65 | 43.05 | 42.6 | 42.65 | 42.55 | 42.6 |
| 95° Ethanol | 45 | 45 | 45 | 45 | 45 | 45 | 45 |

The main differences in the composition of these gels lie in:

the proportions of Nomegestrol acetate (NAc)/Estradiol (E2) used, the choice of absorption-promoting agent («enhancer»), namely Solketal or Transcutol, the respective proportions of PropyleneGlycol (PG)/Solketal, All these gel formulations correspond to the specifications of pH, viscosity, titre and appearance. They are tested in percutaneous passage.

Results of Percutaneous Passage In Vitro

Table 2 below summarises the cumulative quantities (μg) of nomegestrol acetate and estradiol found in the receiving compartment over 24 hours.

TABLE 2

Results of the in vitro cutaneous passage studies on the 1$^{st}$ series gels

| | | G29-287 | G29-299 | Tx11323 batch-12 | C42-110 | G42-111 | G42-112 | G47-1 | G47-5 |
|---|---|---|---|---|---|---|---|---|---|
| NAc (μg) | Av. | 1.253 | 1.741 | — | 2.299 | 2.148 | 1.407 | 1.816 | 1.785 |
| | S.D | 0.791 | 1.216 | — | 0.524 | 1.535 | 1.021 | 1.151 | 0.523 |

TABLE 2-continued

Results of the in vitro cutaneous passage studies on the 1st series gels

|  |  | G29-287 | G29-299 | Tx11323 batch-12 | C42-110 | G42-111 | G42-112 | G47-1 | G47-5 |
|---|---|---|---|---|---|---|---|---|---|
| E2 (µg) | Av. | — | 0.680 | 1.396 | 1.121 | 0.658 | 0.381 | 0.909 | 0.913 |
|  | S.D. | — | 0.149 | 0.653 | 0.257 | 0.469 | 0.276 | 0.614 | 0.258 |

3) Influence of the Presence of Estradiol on the Diffusion of Nomegestrol Acetate

TABLE 3

Comparison of the results of the cutaneous passage of gels G29-287, G29-299 and TX11323

|  |  | G29-287 | G29-299 | Tx11323 batch-12 |
|---|---|---|---|---|
| NAc (µg) | Av. | 1.253 | 1.741 | — |
|  | S.D. | 0.791 | 1.216 | — |
| E2 (µg) | Av. | — | 0.680 | 1.396 |
|  | S.D. | — | 0.149 | 0.653 |

Gels G29-287, G29-299 and TX11323 differ only by the nature of the active ingredient(s) that they contain, the remainder of their composition being strictly identical. Gel G29-287 contains only nomegestrol acetate at 0.40%, Gel TX11323 contains only estradiol at 0.10% and gel G29-299 contains the combination of two active ingredients, nomegestrol acetate and estradiol, at 0.40% and 0.10% respectively.

The best diffusion of nomegestrol acetate towards the receptor cell is obtained for gel G29-299, that is to say for the gel containing nomegestrol acetate combined with estradiol: 1.741 µg of cumulative nomegestrol acetate for gel G29-299 compared with 1.253 µg of cumulative nomegestrol acetate for gel G29-287, i.e. for the gel containing only nomegestrol acetate.

The best diffusion of estradiol is obtained for gel TX11323 (1.396 µg in 24 hours). This gel does not contain nomegestrol acetate, but only estradiol.

It can be concluded that the estradiol encourages the passage of nomegestrol acetate (+39%) whilst nomegestrol acetate partially impedes the percutaneous penetration of the estradiol (−51%)

4) Influence of the Concentration of Estradiol on the Diffusion of Nomegestrol Acetate In order to verify whether the promoter effect of estradiol on the diffusion of nomegestrol acetate was dependant on estrogen concentration, formulations were compared in terms of percutaneous passage, G42-111 containing 0.10% estradiol, G42-110 containing 0.15% estradiol and 47-1 containing 0.20% estradiol. These formulations only differ by their estradiol content.

The results of percutaneous passage in vitro are summarized in Table 4:

TABLE 4

Comparison of the cutaneous passage results of gels G42-111, G42-110 and G47-1

|  |  | G42-111 | G42-110 | G47-1 |
|---|---|---|---|---|
| NAc (µg) | Av. | 2.148 | 2.299 | 1.816 |
|  | S.D. | 1.535 | 0.524 | 1.151 |
| E2 (µg) | Av. | 0.586 | 1.121 | 0.909 |
|  | S.D. | 0.469 | 0.257 | 0.614 |

The best diffusion of nomegestrol acetate in the receiving compartments is obtained for gel G42-110, i.e. for the gel containing 0.15% estradiol: the cumulative quantity of nomegestrol acetate is 2.999 µg for gel G42-110, (0.15% E2) compared with 2.148 µg for gel G42-111 (0.10% E2) and 1.816 µg for gel G47-1 (0.20% E2).

The best diffusion of estradiol is obtained with gel G42-110 (1.121 µg) which produces better results than gel G47-1 (0.909 µg) which itself produces better results than gel G42-111 (0.586 µg). The percutaneous diffusion of estradiol from gels also containing nomegestrol acetate is not therefore proportional to the concentration of estradiol. Therefore, the quantities of estradiol able to diffuse towards the receiving compartment from the gel at 0.15% are greater than those which diffuse from the gels at 0.10% and at 0.20% estradiol.

Conclusion:

Surprisingly, in formulations in which nomegestrol acetate is combined with estradiol, a promoter effect of estradiol on the diffusion of nomegestrol acetate is observed. This promoter effect is revealed with two pairs of different solvents: the propylene-glycol/Transcutol pair (Table 3) and the propylene glycol/Solketal pair (Table 4). Also surprisingly, it has been demonstrated that the promoter effect exercised by estradiol on the diffusion of nomegestrol acetate is not proportional to the concentration of estradiol and that it is maximal for a concentration of estradiol of the order of 0.15%. Conversely, the presence of nomegestrol acetate in the formulation slows the diffusion of estradiol into the receiving compartment in comparison to a gel formulation containing only estradiol.

5) Results Observed In Vivo

The limiting factor, in terms of passage, being nomegestrol acetate, a pharmacokinetic trial was carried out in women with 2 gels containing 0.4% of nomegestrol acetate and taking into account the results previously obtained in vitro. These 2 gels, which differ only by the type of Carbopol used, had compositions with the following percentages:

TABLE 5 formula of the 2 gels used for pharmacokinetic trials in women

|  | Gel A | Gel B |
|---|---|---|
| Nomegestrol acetate | 0.40 | 0.40 |
| Propylene glycol | 8.00 | 8.00 |
| Solketal | 3.00 | 3.00 |
| Carbopol 980 | 0.60 |  |
| Carbopol 1382 |  | 0.50 |
| EDTA | 0.05 | 0.05 |
| TEA | 0.24 | 0.30 |
| 95° Ethanol | 45.00 | 45.00 |
| Demineralized water | 42.69 | 42.73 |

After 3 days administration in 6 menopausal women volunteers (3 g of gel per day, spread over 400 cm$^2$), the average plasmatic levels were equal to:

| Gel A | 0.345 ng/ml |
|---|---|
| Gel B | 0.456 ng/ml |

The kinetic data shows that equilibrium is situated around 0.7 ng/ml. Knowledge of the pharmacokinetics of nomegestrol acetate makes it possible to assert that clinical effectiveness is obtained for plasmatic concentrations equal to or greater than 0.7 ng/ml. Plasmatic levels of the order of 0.7 ng are sufficient to observe an objectivized endometrial effect through bleedings (these results are described in the Patent FR 2.776.191 belonging to the Applicant). Formulations A and B therefore correspond to these aims. However, to ensure a complete therapeutic effect in all women it would be worthwhile obtaining higher circulating levels of nomegestrol acetate. Surprisingly, it was possible to further improve the results of diffusion in vitro by the perfection of other formulations.

Gel B was previously tested in vitro using the same method as that used in the study of gels in combination. The results of percutaneous passage over 24 hours are shown in Table 6:

TABLE 6

Results of cutaneous passage of the Gel B type formulation

|  |  | Gel B |
|---|---|---|
| NAc (µg) | Av. | 1.662 |
|  | S.D. | 0.649 |

Therefore, in vitro and under the operating conditions used for these tests, diffusion into the receiving compartment of 1.66 µg of NAc makes it possible to obtain a plasmatic level at equilibrium in the order of 0.7 ng/ml.

The nomegestrol acetate gels likely to give satisfactory clinical results must therefore present, during the tests of percutaneous passage in vitro, cumulative quantities of nomegestrol acetate over 24 hours of greater than 1.66 µg.

In the same way, gel TX11323, applied at a rate of 3 g of gel on a body area of 400 cm$^2$ leads to plasmatic levels of estradiol at the equilibrium of approximately 40 pg/ml, which are located in the area of effective plasmatic concentrations of estradiol as these are comprised between 30 and 60 ng/ml.

Therefore, in vitro, diffusion into the receiving compartment of 1.40 µg over 24 hours (Table 2), leads of the plasmatic levels of estradiol at equilibrium, of the order of 40 pg/ml. Estradiol gels likely to produce satisfactory clinical results must therefore present during the tests of percutaneous passage, cumulative quantities of estradiol at 24 hours of greater than 1.05 µg without however exceeding 2.1 µg so as not to induce hyperestrogenosis.

A new series of gels has therefore been manufactured in order to confirm the first results obtained, and in particular the promoter effect exercised by estradiol on the cutaneous absorption of nomegestrol acetate and to study the combined action of other absorption promoting agents.

6) Study of Other Families of Absorption Promoting Agents (2$^{nd}$ Series of Gels)

The percutaneous passage of the two active ingredients was studied in vitro in gel formulations differing only by the nature of the absorption promoter used, the other elements of the formulation remaining identical:

TABLE 7

Type of formulation of gels containing other families of absorption promoting agents (2$^{nd}$ series of gels).

| Constituents | Percentage in the formula |
|---|---|
| Nomegestrol acetate (NAc) | 0.42 |
| Estradiol | 0.15 |
| Carbopol 1382 | 0.50 |
| Propylene Glycol | 8.0 |
| Absorption promoter | 3.00 |
| EDTA | 0.05 |
| TEA | 0.30 |
| 95° Ethanol | 45.00 |
| Demineralised water | 42.58 |

The formulations corresponding to this basic formulation are summarized below:

TABLE 8

Absorption promoting agents tested.

| Chemical family | Chemical name | Trade name | Formulation Ref. |
|---|---|---|---|
| Polyols | Propylene glycol monocaprylate | Capryol 90 | G49-80 |
|  | PEG-6 caprylic/capric glycerides | Softigen 767 | G49-88 |
|  | PEG-7 glyceryl cocoate | Cetiol HE | G49-102 |
|  | PPG-5 ceteth-20 | Procetyl AWS | G49-110 |
| Fatty acid | Octanoic acid | Caprylic acid | G49-100 |
|  | Octadec 9-enoic acid | Oleic acid | G49-106 |
|  | Dodecanoic acid | Lauric acid | G49-108 |
| Fatty acid esters | Diisopropyl adipate | Crodamol DA | G49-90 |
| Surfactants | Polysorbate 80 | Montanox 80 | G49-82 |
|  | Popylene glycol dicaprylate/caprate | Mygliol 840 | G49-111 |
| Alcohols | 2-Octyl dodecanol | Eutanol 6 | G49-104 |
| Amides | 1-dodecylazacyclohepta-2-one | Azone | G49-139 |

In another formulation with the reference G42-120, a silicone DC Blend 20 is added to the gel with the reference G42-110 (Solketal 3%), at the rate of 2% by weight of the formulation.

These formulations were also compared to a control formulation (an identical formula but not containing an absorption promoting agent: Ref. G49-114).

The formula corresponding to this gel is shown in Table 9.

TABLE 9

Composition of gel G49-114

| Constituents | Reference G49-114 (control) |
|---|---|
| Nomegestrol acetate | 0.42 |
| Estradiol | 0.15 |
| Carbopol 1382 | 0.50 |
| Propylene Glycol | 8.00 |
| Absorption promoter | — |
| EDTA | 0.05 |
| TEA | 0.30 |
| 95° Ethanol | 45.00 |
| Demineralised water | 45.58 |

Results in Vitro:

The in vitro results obtained with these formulations and expressed as cumulative quantities of active ingredients having diffused into the receiving compartment over 24 hours, are summarized in tables 10a and 10b:

Tables 10a and 10b: Results of the Studies of Cutaneous Passage Carried Out on the $2^{nd}$ Series of Gels TABLE 10a

| | | G49-114 | G49-80 | G49-88 | G49-102 | G49-110 | G49-100 | G49-106 | G49-108 |
|---|---|---|---|---|---|---|---|---|---|
| NAc (µg) | Av. | 1.368 | 1.468 | 1.400 | 1.053 | 0.576 | 3.820 | 1.988 | 3.761 |
| | S.D. | 0.508 | 0.646 | 0.307 | 0.527 | 0.102 | 1.179 | 0.814 | 0.437 |
| E2 (µg) | Av. | 0.698 | 0.732 | 0.984 | 0.307 | 0.13 | 1.91 | 1.527 | 2.308 |
| | S.D. | 0.247 | 0.320 | 0.220 | 0.181 | 0.029 | 0.503 | 0.554 | 0.304 |

TABLE 10b

| | | G49-82 | G49-111 | G49-104 | G49-139 | G49-90 | G42-120 |
|---|---|---|---|---|---|---|---|
| NAc (µg) | Av. | 1.099 | 1.572 | 1.514 | 1.352 | 0.788 | 2.782 |
| | S.D. | 0.310 | 0.358 | 0.548 | 0.465 | 0.178 | 1.068 |
| E2 (µg) | Av. | 0.303 | 1.217 | 0.700 | 0.173 | 0.235 | 1.368 |
| | S.D. | 0.104 | 0.313 | 0.318 | 0.044 | 0.124 | 0.562 |

Figure 1:
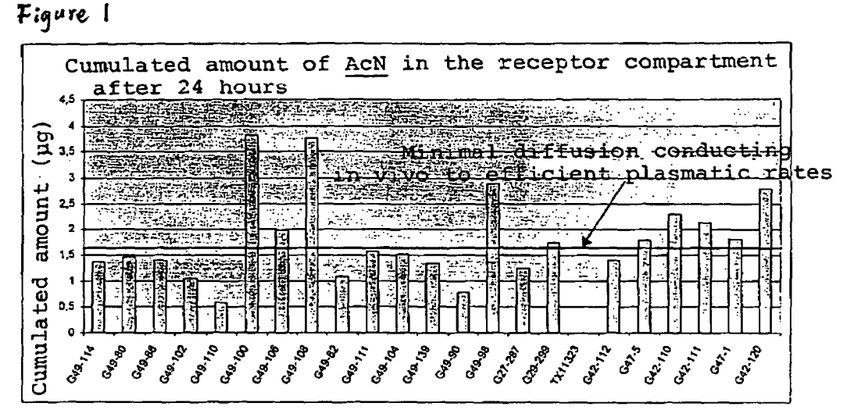
FIG. 1 is a graph of the cumulated amount of AcN in the receptor component after 24 hours.
Figure 2:
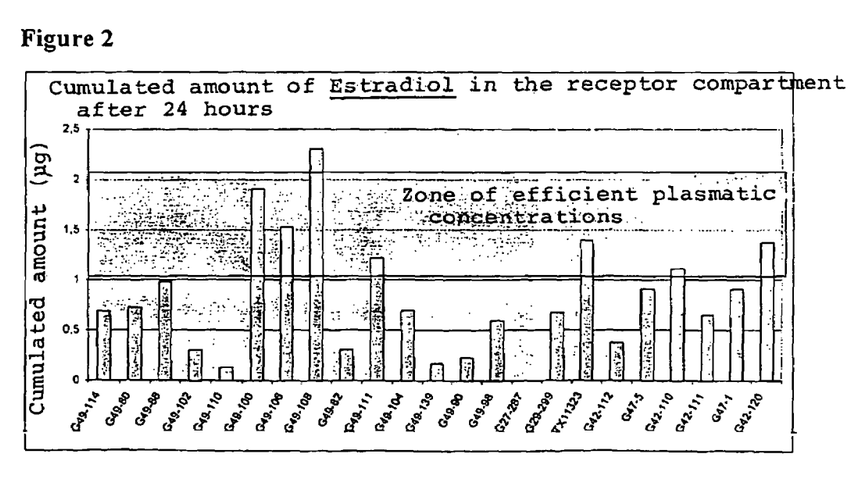
FIG. 2 is a graph of the cumulated amount of estradiol in the receptor component after 24 hours.

Analysis of the results shown in FIGS. 1 and 2 shows that the diffusible quantities of nomegestrol acetate and estradiol can be adjusted, by choosing the nature of absorption promoter used. When the quantities of active ingredients having diffused into the receiving compartment from formulations containing an absorption promoter are compared to those observed with the control formulation, it can be noted that certain promoters exclusively favoured the diffusion of estradiol without affecting the diffusion of nomegestrol acetate. This phenomenon is observed with Softigen 767 (G49-88) and Miglyol 840 (G49-111). Other promoters encourage the passage of the two active ingredients in a simultaneous manner. This is the case for long chain fatty acids (G49-100, G49-106 and G49-108), and Solketal-based formulations G42-110 and G42-120. None of the promoters currently studied is capable of exclusively promoting the passage of nomegestrol acetate.

Surprisingly, it has been observed that certain excipients, traditionally described as absorption promoting agents, on the contrary slow the diffusion of the active ingredients(s). Thus, Azone, (gel reference G49-139), significantly reduces the diffusion of estradiol towards the receiving compartment and has no effect on the diffusion of the nomegestrol acetate. Cetiol HE (G49-102), Procetyl AWS (G49-110), Montanox 80 (G49-82) and Crodamol DA (G49-90) provoke a significant reduction in the diffusion of the two active ingredients in comparison to the formulation which does not contain absorption promoter. Therefore, the nature of the absorption promoting agent capable of improving the simultaneous passage of nomegestrol acetate and estradiol does not appear to have been anticipated. Nevertheless, it can be noted from previously established in vitro/in-vivo correlations, that some formulations make it possible to ensure both an effective plasmatic level of nomegestrol acetate and an effective plasmatic level of estradiol, despite the previously described competition in terms of percutaneous passage between the two molecules. In particular it concerns the formulations with references G42-120, G49-106, G49-108 and G49-100. Some of these formulations contain promoters known to be badly tolerated by the skin and must be used with caution. This is why formulation G42-120, which contains a film-forming agent combined with other excipients, the harmlessness of which has been thoroughly demonstrated, will be that which will be preferably used.

7) Role of the Film-Forming Agent

TABLE 11

Comparison of the results of the cutaneous passage of gels G42-110 and G42-120

| | | G42-110 | G42-120 |
|---|---|---|---|
| NAc (µg) | Av. | 2.299 | 2.782 |
| | S.D. | 0.524 | 1.068 |

TABLE 11-continued

Comparison of the results of the cutaneous passage of gels G42-110 and G42-120

|   |      | G42-110 | G42-120 |
|---|------|---------|---------|
| E2 (μg) | Av. | 1.121 | 1.368 |
|   | S.D. | 0.257 | 0.562 |

The only difference between gels G42-110 and G42-120 lies in the addition of a film-forming agent (silicone DC Blend 20) in the second. These 2 gels contain 8% Propylene glycol (PG) and 3% Solketal (S).

The strongest diffusion of nomegestrol acetate is obtained with gel G42-120: the cumulative quantity of nomegestrol acetate having diffused over a period of 24 hours, is 2.782 μg for gel G42-120 against 2.299 μg for gel G42-110, which represents an increase of more than 20% of the diffusion of nomegestrol acetate.

Similarly, the estradiol diffuses better through the skin with gel G42-120: the cumulative quantity of estradiol, over a period of 24 hours, is 1.368 μg for gel G42-120 against 1.121 μg for gel G42-110, which also represents an increase of more than 20% of the diffusion of estradiol.

8) Influence of the Concentration of Nomegestrol Acetate on Diffusion In Vitro

All the previous tests having been carried out on formulations of 0.4% nomegestrol acetate, the study of the influence on percutaneous diffusion of nomegestrol acetate concentration in the gel was required. Given the good results obtained with gel G42-110 in the previous passage studies, this formulation was used as a starting point. In order to make it possible to dissolve larger quantities of nomegestrol acetate, the concentrations of Solketal and alcohol which are excellent solvents for this active ingredient were increased. Finally, to maintain the same viscosity of these gels compared to gel G42-110, the concentration of Carbopol was also increased. The formulations are shown in Table 12.

TABLE 12

Composition in percentages of the gels

|   | G42-110 | G52-289 | G52-290 |
|---|---------|---------|---------|
| NAc | 0.4 | 1.00 | 1.7 |
| Estradiol | 0.15 | 0.15 | 0.15 |
| Carbopol 1382 | 0.5 | 0.7 | 0.7 |
| Propylene glycol | 8 | 8 | 8 |
| Solketal | 3 | 6 | 6 |
| EDTA | 0.05 | 0.05 | 0.05 |
| Triethanolamine | 0.3 | 0.3 | 0.3 |
| Demineralized water | 42.6 | 28.8 | 28.1 |
| 95° Ethanol | 45 | 55 | 55 |

Results of percutaneous passage in vitro

Table 13 below summarizes the cumulative quantities (μg) of nomegestrol acetate found in the receiving compartment over 24 hours.

TABLE 13

Results of the studies of cutaneous passage in vitro on the gels with different concentrations of nomegestrol acetate

|   | G42-110* | G52-289 | G52-290 |
|---|----------|---------|---------|
| Conc NAc | 0.4 | 1.0 | 1.7 |
| NAc (μg) | 2.30* | 2.93 | 4.68 | cumulative quantities (μg) of nomegestrol acetate found in the receiving compartments over 24 hours.
*result obtained in the 1st series tests It has previously been shown that nomegestrol acetate gels, which are capable of giving satisfactory clinical results, must present, during the tests of percutaneous passage in vitro, cumulative quantities of nomegestrol acetate of greater than 1.66 μg at 24 hours.

The results of Table 13 show that, in a suitable formulation, gels with concentrations of nomegestrol acetate ranging from 0.4 to 1.7% deliver cumulative quantities of nomegestrol acetate much greater than 1.66 μg at 24 hours and are therefore capable of giving satisfactory clinical results. It has also been noted that the quantity of active ingredient which passes through the skin increases as a function of its concentration in the gel.

9) Role of the <<Solubilizing Agent/Promoter Agent>> Proportion

Table 14 below shows the results of passage in vitro expressed in cumulative quantities at 24 hours observed in formulations G42-110 and G47-5 of the first series of gels with 0.4% nomegestrol acetate which only differs in the choice of the proportions of Propylene glycol (PG)/Solketal (S), which are 8/3 for gel G42-110 and 6/5 for gel G47-5 respectively.

TABLE 14

Comparison of the results of the cutaneous passage of gels G42-110 and G47-5

|   |      | G42-110 | G47-5 |
|---|------|---------|-------|
| NAc (μg) | Av. | 2.299 | 1.785 |
|   | S.D. | 0.524 | 0.523 |
| E2 (μg) | Av. | 1.121 | 0.913 |
|   | S.D. | 0.257 | 0.258 |

Gel G42-110 allows better diffusion of nomegestrol acetate than gel G47-5: 2.299 μg of cumulative NAc for gel G42-110 compared with 1.785 μg for gel G47-5 is obtained.

Similarly, gel G42-110 also allows better diffusion of estradiol (E2) than gel G47-5: 1.121 μg of cumulative E2 for gel G42-110 compared with 0.913 μg for gel G47-5 is obtained. Therefore, for this type of formulation, it is more advantageous to use the PG/S system in the proportions of 8/3 rather than 6/5.

In another series of tests, the influence of the propylene glycol/solketal pair on the percutaneous passage of gels which a higher concentration of nomegestrol acetate, i.e. at 1.0% was studied.

TABLE 15

Composition in percentages of the gels

|  | G235-001 | G52-289 | G52-292 |
|---|---|---|---|
| NAc | 1.00 | 1.00 | 1.00 |
| Estradiol | 0.15 | 0.15 | 0.15 |
| Carbopol 1382 | 0.7 | 0.7 | 0.7 |
| Propylene glycol | 8 | 8 | 3 |
| Solketal | 3 | 6 | 11 |
| EDTA | 0.05 | 0.05 | 0.05 |
| Triethanolamine | 0.3 | 0.3 | 0.3 |
| Demineralised water | 31.8 | 28.8 | 28.8 |
| 95° Ethanol | 55 | 55 | 55 |

These formulations only differ in the proportions of the propylene glycol/solketal mixture.

TABLE 16

Results of the studies of cutaneous passage in vitro on the gels in different proportions of propylene glycol/solketal

|  | G235-001 | G52-289 | G52-292 |
|---|---|---|---|
| Propylene glycol | 8 | 8 | 3 |
| Solketal | 3 | 6 | 11 |
| NAc (µg) | 3.17 | 2.93 | 1.61 |
| E2 (µg) | 0.71 | 0.64 | 0.32 |

Surprisingly, it has been noted that, for these formulations, increasing the concentration of the promoter agent, Solketal, induces a reduction in the level of the two hormones passing through.

The results of these two series of trials shows that for each formulation, the optimal proportion of solubilizing agent and absorption promoter cannot be known in advance and must be studied case by case.

10) Conclusion

Trials of this invention attest that the concentration of each component and its interaction with the other components of a cutaneous gel formulation can, surprisingly, lead to a synergy or, on the contrary, to an inhibition of the quantity of active ingredients which pass through by the percutaneous route. Because of this, the preparations previously described for the percutaneous passage of a synthetic progestogen on its own, as described, are not directly applicable to an estrogen-progestogen combination as each combination of this type requires a specific galenic solution.

In particular:

Estradiol, used in certain concentrations, can encourage the percutaneous passage of nomegestrol acetate;

nomegestrol acetate, in general, reduces the percutaneous passage of estradiol;

the nature of the absorption promoter ensuring adequate percutaneous passage for each active ingredient is not foreseeable;

among the absorption promoting agents, dioxanes (such as Solketal and SEPA) and long chain fatty acids are those which make it possible to better attain the objectives;

the optimal ratio between the solvent and the passage promoter must be determined for each formulation;

the addition of a film-forming agent such as silicone DC Blend 20, makes it possible to increase the percutaneous passage of the active ingredients, nomegestrol acetate and estradiol, by approximately 20% whilst improving the cosmetic characteristics of the composition.

Formulations containing long chain fatty acids such as caprylic acid, oleic acid or lauric acid are also favourably retained.

We claim:

1. A topical composition with a systemic effect, for the hormonal treatment of the perimenopause and of the menopause as well as for the treatment of ovarian hormonal deficiencies in women with amenorrhea, based on a progestogen and an oestrogen agent, comprising
    as active ingredientss, nomegestrol and/or one of its esters or its ethers and estradiol and/or one of its esters or its ethers,
    and a vehicle allowing the systemic passage of said active ingredients, selected from the group consisting of a solubilizing agent, an absorption agent, a film-forming agent, a gelling agent and their mixture,
in combination or in admixture with suitable excipients for the realization of a pharmaceutical, gelled and/or film-forming agent.

2. A topical hormonal composition with a systemic effect of claim 1, wherein the progestogen derived from 19-nor progesterone is nomegestrol acetate.

3. A topical composition with a systemic effect of claim 1, wherein the oestrogen is a fatty acid ester of estradiol.

4. A topical composition with a systemic effect of claim 1, wherein the oestrogen is an estradiol ether.

5. A topical hormonal composition with a systemic effect of claim 1, wherein the amount of nomegestrol or of one of its esters or ethers ranges from 0.05 to 5.0% by weight of the total composition.

6. A topical hormonal composition with a systemic effect of claim 5, wherein the amount of nomegestrol or of one of its esters or ethers is about 1.0% by weight of the total composition.

7. A topical hormonal composition with a systemic effect of claim 1, wherein the amount of estradiol or of one of its esters or ethers is 0.05 to 1.0% by weight of the total composition.

8. A topical hormonal composition with a systemic effect of claim 7, wherein the amount of estradiol or of one of its esters or ethers is about 0.15% by weight of the total composition.

9. A topical hormonal composition with a systemic effect of claim 1, wherein the solubilizing agent is selected from the group consisting of alcohols, water-alcohol mixtures, propyleneglycol and their mixtures.

10. A topical hormonal composition with a systemic effect of claim 1, wherein the solubilizing agent is an ethanol/water/propyleneglycol ternary mixture, in which the amount of ethanol is 30 to 60% by weight of the total composition and that of propyleneglycol is 2 to 20% by weight of the total composition.

11. A topical hormonal composition with a systemic effect of claim 1, wherein the absorption promoting agent is selected from the group consisting of dioxolanes and long chain fatty acids of 6 to 18 carbon atoms.

12. A topical hormonal composition with a systemic effect of claim 11, wherein the absorption promoting agent is 2 to 12% by weight of the total composition.

13. A topical hormonal composition with a systemic effect of claim 11, wherein the absorption promoting agent is isopropylideneglycerol or 2 n-nonyl 1,3-dioxolane.

14. A topical hormonal composition with a systemic effect of claim 1, wherein the gelling agent is selected from the group consisting of cellulose derivatives and acrylic derivatives.

15. A topical hormonal composition with a systemic effect of claim 14, wherein the acrylic derivatives is a carbomer used at a concentration of 0.3 to 1% by weight of the total composition.

16. A topical hormonal composition with a systemic effect of claim 1, wherein the film-forming agent is chosen from the group consisting of silicones, cellulose derivatives, methacrylic derivatives and polyvinylpyrrolidone derivatives.

17. A topical hormonal composition with a systemic effect of claim 16, wherein the silicone is selected from the group consisting of dimethicone, dimethiconol simethicone and their mixtures.

18. A topical hormonal composition with a systemic effect of claim 16, wherein the silicone is a mixture formed from the dimethiconol in dimethicone.

19. A topical hormonal composition with a systemic effect of claim 17, wherein the amount of silicone is 1 to 3% by weight of total composition.

20. A topical hormonal composition of claim 1, in the form of a penetrating gel, wherein it contains, in a hydroalcoholic mixture, 0.4% nomegestrol acetate, 0.15% estradiol, 8% propyleneglycol, 3% isopropylideneglycerol and 2% of a mixture formed from dimethiconol in dimethicone.

21. A topical hormonal composition of claim 1, in the form of a penetrating gel, wherein it contains, in a hydroalcoholic mixture, 0.4% nomegestrol acetate, 0.15% estradiol, 8% propyleneglycol, 3% long chain fatty acids and 2% of a mixture formed from dimethiconol in dimethicone.

22. A topical hormonal composition of claim 1, wherein it contains, in the form of a penetrating gel, in a hydroalcoholic mixture, 0.4% nomegestrol acetate, 0.15% estradiol, approximately 8% propyleneglycol and approximately 3% isopropylideneglycerol.

23. A topical hormonal composition of claim 1, in the form of a penetrating gel containing a hydroalcoholic mixture, wherein 0.4% nomegestrol acetate, 0.15% estradiol, approximately 8% propyleneglycol, and approximately 3% long chain fatty acids.

24. A topical hormonal composition of claim 3 wherein the fatty acid esters of estradiol is estradiol valerate.

25. A topical hormonal composition of claim 4 wherein the ether is promestriene.

* * * * *